US010052047B2

(12) United States Patent
Feger et al.

(10) Patent No.: US 10,052,047 B2
(45) Date of Patent: Aug. 21, 2018

(54) SYSTEM AND METHOD FOR FUNCTIONAL GAIT RE-TRAINER FOR LOWER EXTREMITY PATHOLOGY

(71) Applicant: University of Virginia Patent Foundation, Charlottesville, VA (US)

(72) Inventors: Mark Feger, Richmond, VA (US); Jay N. Hertel, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/228,618

(22) Filed: Aug. 4, 2016

(65) Prior Publication Data
US 2017/0035641 A1 Feb. 9, 2017

Related U.S. Application Data

(60) Provisional application No. 62/202,472, filed on Aug. 7, 2015, provisional application No. 62/368,463, filed on Jul. 29, 2016.

(51) Int. Cl.
*A63B 24/00* (2006.01)
*A61B 5/11* (2006.01)
(Continued)

(52) U.S. Cl.
CPC ............ *A61B 5/112* (2013.01); *A61B 5/1038* (2013.01); *A61H 1/0255* (2013.01);
(Continued)

(58) Field of Classification Search
CPC . A63B 24/00; A63B 24/0062; A63B 24/0087; A63B 22/0292; A63B 22/0235; A63B 69/0059; A63B 21/0442; A63B 21/0552; A63B 21/00061; A63B 21/4034; A63B 21/4013; A63B 21/0428; A63B 23/03541; A63B 23/0405; A63B 2225/50; A63B 2230/60; A63B 2220/36; A63B 2220/40; A61B 5/112; A61B 5/1038; A61H 1/0255; A61H 2201/0119; A61H 2201/1261; A61H 2201/164;
(Continued)

(56) References Cited

U.S. PATENT DOCUMENTS 6,666,831 B1 * 12/2003 Edgerton ............. A61H 1/0237
600/587
7,455,620 B2 11/2008 Frykman
(Continued)

OTHER PUBLICATIONS

Arnold, B.L et al., "Concentric Evertor Strength Differences and Functional Ankle Instability: A Meta-Analysis", Journal of Athletic Training. 2009, pp. 653-662, vol. 44, No. 6.
(Continued)

*Primary Examiner* — Glenn Richman
(74) *Attorney, Agent, or Firm* — Robert J. Decker

(57) ABSTRACT

A gait device and method for rehabilitating or developing a subject's lower extremity. The device may include a movable belt configured for the subject to ambulate thereon; a track provided above the movable belt that is generally aligned with the movable belt; and a coupler that is configured to travel along the track and attach to the distal portion of the lower extremity of the subject while the subject is ambulating on the movable belt.

9 Claims, 8 Drawing Sheets

(51) Int. Cl.
 A63B 22/02 (2006.01)
 A61B 5/103 (2006.01)
 A63B 69/00 (2006.01)
 A61H 1/02 (2006.01)
 A63B 21/055 (2006.01)
 G06F 19/00 (2018.01)
 A63B 21/04 (2006.01)
 A63B 23/035 (2006.01)
 A63B 23/04 (2006.01)
 A63B 21/00 (2006.01)
(52) U.S. Cl.
 CPC ...... *A63B 21/0552* (2013.01); *A63B 21/4045* (2015.10); *A63B 22/0235* (2013.01); *A63B 69/0059* (2013.01); *G06F 19/3481* (2013.01); *A61H 2201/0119* (2013.01); *A61H 2201/1261* (2013.01); *A61H 2201/164* (2013.01); *A61H 2201/165* (2013.01); *A61H 2201/1645* (2013.01); *A61H 2201/5097* (2013.01); *A61H 2230/60* (2013.01); *A63B 21/00061* (2013.01); *A63B 21/0428* (2013.01); *A63B 21/0442* (2013.01); *A63B 21/4013* (2015.10); *A63B 21/4034* (2015.10); *A63B 23/03541* (2013.01); *A63B 23/0405* (2013.01); *A63B 2069/0062* (2013.01); *A63B 2220/30* (2013.01); *A63B 2220/36* (2013.01); *A63B 2220/40* (2013.01); *A63B 2220/56* (2013.01); *A63B 2220/806* (2013.01); *A63B 2220/836* (2013.01); *A63B 2225/50* (2013.01); *A63B 2230/60* (2013.01)
(58) Field of Classification Search
 CPC ...... A61H 2201/1645; A61H 2201/165; A61H 2201/5097; A61H 2230/60; G06F 19/3481
 See application file for complete search history.

(56) References Cited

U.S. PATENT DOCUMENTS

| | | | |
|---|---|---|---|
| 8,308,618 | B2 | 11/2012 | Bayerlein |
| 8,628,485 | B2 | 1/2014 | Wilson |
| 8,920,347 | B2 | 12/2014 | Bayerlein |
| 9,084,712 | B2 | 7/2015 | Roerdink |
| 9,186,552 | B1 | 11/2015 | Deal |
| 9,713,439 | B1* | 7/2017 | Wu .......................... A61B 5/11 |
| 9,757,610 | B2* | 9/2017 | Artemiadis ........ A63B 22/0292 |
| 2004/0192511 | A1 | 9/2004 | Ein-Gal |
| 2008/0070757 | A1 | 3/2008 | Albert |
| 2008/0234113 | A1 | 9/2008 | Einav |
| 2010/0035727 | A1 | 2/2010 | Brunner |
| 2010/0152629 | A1 | 6/2010 | Haas, Jr. |
| 2013/0324888 | A1 | 12/2013 | Solinsky |
| 2015/0087484 | A1* | 3/2015 | Bayerlein .......... A63B 22/0235 482/54 |
| 2016/0074272 | A1 | 3/2016 | Ahn |

OTHER PUBLICATIONS

Carcia, C.A., et al., "Validity of the Foot and Ankle Ability Measure in Athletes With Chronic Ankle Instability", Journal of Athletic Training. 2008, pp. 179-183, vol. 43, No. 2.
Cohen, J., "Statistical Power Analysis for the Behavioral Sciences", Second Edition, 1988, 41 pages, Lawrence Erlbaum Associates.
Delahunt, E., et al., "Altered Neuromuscular Control and Ankle Joint Kinematics During Walking in Subjects With Functional Instability of the Ankle Joint", The American Journal of Sports Medicine, 2006, pp. 1970-1976, vol. 34, No. 12.
Docherty, C.L., et al., "Effects of Strength Training on Strength Development and Joint Position Sense in Functionally Unstable Ankles", Journal of Athletic Training, Dec. 1998, pp. 310-314, vol. 33, No. 4.
Donahue, M., et al., "Reliability and Validity of a New Questionnaire Created to Establish the Presence of Functional Ankle Instability: The IdFAI", Athletic Training and Sports Health Care, 2013, pp. 38-43, vol. 5, No. 1.
Donovan L., et al., "A New Paradigm for Rehabilitation of Patients With Chronic Ankle Instability", The Physician and Sportsmedicine, Nov. 2012, pp. 41-51, vol. 40, Iss. 4.
Donovan, L., et al., "Effects of ankle destabilization devices and rehabilitation on gait biomechanics in chronic ankle instability patients: A randomized controlled trial", Physical Therapy in Sport, 2016, pp. 46-56, vol. 21.
Donovan, L., et al., "Rehabilitation for Chronic Ankle Instability With and Without Destabilization Devices: A Randomized Controlled Trial", Journal of Athletic Training, Mar. 2016, pp. 233-251, vol. 51, No. 3.
Drewes, L.K., et al., "Altered Ankle Kinematics and Shank-Rear-Foot Coupling in Those With Chronic Ankle Instability", Journal of Sport Rehabilitation, 2009, pp. 375-388, vol. 18, No. 3.
Feger M., et al., "Lower Extremity Muscle Activation in Patients With and Without Chronic Ankle Instability", Journal of Athletic Training, 2015, pp. 350-357, vol. 50, No. 4.
Feger M.A., et al., "Surface electromyography and plantar pressure changes with novel gait training device in participants with chronic ankle instability", Clinical Biomechanis, 2016, pp. 117-124, vol. 37.
Gerber, J.P., et al., "Persistent Disability Associated with Ankle Sprains: A Prospective Examination of an Athletic Population", Foot & Ankle International, Oct. 1998, pp. 653-660, vol. 19, No. 10.
Godin, G., et al., "Assessment of Leisure Time Exercise Behavior by Self-Report: A Concurrent Validity Study," Canadian Journal of Public Health, 1986, pp. 359-362, vol. 77, No. 5.
Gribble, P.A., et al., "Selection Criteria for Patients With Chronic Ankle Instability in Controlled Research: A Position Statement of the International Ankle Consortium", Journal of Orthopaedic & Sports Physical Therapy, Aug. 2013, pp. 585-591, vol. 43, No. 8.
Hertel, J., "Sensorimotor Deficits with Ankle Sprains and Chronic Ankle Instability", Clinics in Sports Medicine, 2008, pp. 353-370, vol. 27, No. 3.
Hiller, C.E., et al., "Characteristics of people with recurrent ankle sprains: A systematic review with meta-analysis", British Journal of Sports Medicine, 2011, pp. 660-672, vol. 45, No. 8.
Hoch, M.C., "Joint Mobilization Improves Spatiotemporal Postural Control and Range of Motion in Those with Chronic Ankle Instability", Journal of Orthopaedic Research, Mar. 2011, pp. 326-332, vol. 29, No. 3.
Holmes, A. et al., "Treatment of Common Deficits Associated with Chronic Ankle Instability", Sports Medicine, 2009, pp. 207-224, vol. 39, No. 3.
Hopkins, J.T., et al., "Alterations in evertor/invertor muscle activation and center of pressure trajectory in participants with functional ankle instability", Journal of Electromyography and Kinesiology, 2012, pp. 280-285, vol. 22, No. 2.
Hopkins, W., et al., "Progressive Statistics for Studies in Sports Medicine and Exercise Science", Medicine and Science in Sports Exercise, Jan. 2009, pp. 3-12, vol. 41, Iss. 1.
Koldenhoven, R.M., et al., "Surface electromyography and plantar pressure during walking in young adults with chronic ankle instability", Knee Surgery, Sports Traumatology, Arthroscopy, 2016, pp. 1060-1070, vol. 24.
Martin, R.L., et al., "Evidence of Validity for the Foot and Ankle Ability Measure (FRAM)", Foot & Ankle International, Nov. 2005, pp. 968-983, vol. 26, No. 11.
Mickeon, P., et al., "Balance Training Improves Function and Postural Control in Those with Chronic Ankle Instability", Medicine and Science in Sports and Exercise, 2008, pp. 1810-1819, vol. 40, No. 10.
Mickeon, P.O., et al., "Effects of balance training on gait parameters in patients with chronic ankle instability: A randomized controlled trial", Clinical Rehabilitation, 2009, pp. 609-621, vol. 23, No. 7.
Morrison, K.E., et al., "Plantar Pressure During Running in Subjects With Chronic Ankle Instability", Foot & Ankle International, 2010, pp. 994-1000, vol. 31, No. 11.
Nawata, K.K., "Plantar pressure distribution during gait in athletes with functional instability of the ankle joint: Preliminary report",

(56) References Cited

OTHER PUBLICATIONS

Journal of Orthopaedic Science: The Japanese Orthopaedic Association, 2005, pp. 298-301, vol. 10, No. 3.
Rice, H., et al., "High medial plantar pressures during barefoot running are associated with increased risk of ankle nversion injury in Royal Marine recruits", Gait & Posture, 2013, pp. 614-618, vol. 38, No. 4.
Schmidt, H., et al., "Increased In-Shoe Lateral Plantar Pressures With Chronic Ankle Instability", Foot & Ankle International, Nov. 2011, pp. 1075-1080, vol. 32, No. 11.
Sekir, U., "Effect of isokinetic training on strength, functionality and proprioception in athletes with functional ankle instability", Knee Surgery, Sports Traumatology, Arthroscopy, 2007, pp. 654-664, vol. 15, No. 5.
Terada, M., "Therapeutic Interventions for Increasing Ankle Dorsiflexion After Ankle Sprain: A Systematic Review", Journal of Athletic Training, Oct. 2013, pp. 696-709, vol. 48, No. 5.
Van Rijn, R.M., et al., "What is the Clinical Course of Acute Ankle Sprains? A Systematic Literature Review", The American Journal of Medicine, Apr. 2008, pp. 324-331; 331.e1-331.e7, vol. 121, No. 4.
Verhagen, R.A., et al., "Long-term follow-up of inversion trauma of the ankle", Archives of Orthopaedic and Trauma Surgery, 1995, pp. 92-96, vol. 114, No. 2.
Vicenzino, B., et al., "Initial Changes in Posterior Talar Glide and Dorsiflexion of the Ankle After Mobilization With Movement in Individuals With Recurrent Ankle Sprain", Journal of Orthopaedic & Sports Physical Therapy, Jul. 2006, pp. 464-471, vol. 36, No. 7.
Waterman, B.R., et al., "The Epidemiology of Ankle Sprains in the United States", Journal of Bone and Joint Surgery American, Oct. 2010, pp. 2279-2284, vol. 92-A, No. 13.
Willems, T., et al., "Relationship between gait biomechanics and inversion sprains: a prospective study of risk factors", Gait and Posture, 2005, pp. 379-387, vol. 21, No. 4.

\* cited by examiner

SYSTEM AND METHOD FOR FUNCTIONAL GAIT RE-TRAINER FOR LOWER EXTREMITY PATHOLOGY

RELATED APPLICATIONS

The present application claims priority of priority under 35 U.S.C. § 119 (e) from U.S. Provisional Application Ser. No. 62/202,472, filed Aug. 7, 2015, entitled "System And Method for Functional Gait Re-Trainer For Lower Extremity Pathology," and U.S. Provisional Application Ser. No. 62/368,463, filed Jul. 29, 2016, entitled "System And Method for Functional Gait Re-Trainer For Lower Extremity Pathology,"; the disclosures of which are hereby incorporated by reference herein in their entirety.

FIELD OF THE INVENTION

The present invention relates generally to the field of improving gait and/or strengthening lower limb muscles (for example, knee, ankle, and hip muscles) for rehabilitation and conditioning.

BACKGROUND

Many acute and chronic lower extremity musculoskeletal injuries are a result of improper lower extremity mechanics during exercise. Strengthening of the knee, hip, and ankle muscles are traditionally a cornerstone of lower extremity rehabilitation, as these muscles control most of the gait. The present inventors recognize that the standard exercises for strengthening these muscles during rehabilitation are non-functional, which means they have little translational value to improving gait while running, walking, or jogging and, thus, do not entirely solve the problem. Therefore, the present inventors submit that there is a need for a functional way to strengthen lower limb muscles (for example knee, ankle, and hip muscles) for rehabilitation of a lower extremity injury while improving gait.

Overview

An aspect of an embodiment of the present invention provides, among other things, a prophylactic and rehabilitative gait re-training device and related method for use on any motorized treadmill or the like. An aspect of an embodiment of the gait re-trainer (device and related method) allows patients (or other users and athletes) to, among other things, rehabilitate (and/or condition) through functional exercises while doing cardiovascular and musculoskeletal training on a progressive and personalized program.

An aspect of an embodiment of the present invention provides, among other things, a gait re-trainer apparatus and method for lower extremity pathology for use on any motorized treadmill. While a patient walks, jogs, or runs, an embodiment of the present invention re-training device applies a medial force via elastic bands to each lower extremity independently with the goal of strengthening ankle, knee, and hip muscles in a functional and translational way. The elastic bands have varying degrees of resistance from low to high so they can be retrofitted for each patient's individual rehabilitation needs (or athlete's or user's conditioning). The varying degrees of resistance also allow a patient to progress through the rehabilitation program by steadily increasing their resistance. The lower extremity is considered to be inclusive of the following analogous terms: lower limb, lower member; inferior member or inferior limb. The lower extremity includes: hip, hip joint, thigh, knee, leg, ankle and foot.

An aspect of an embodiment of the present invention provides, among other things, a novel gait training device and related method thereof. The device (and related method) was designed for use with a treadmill and was developed to target activation of the hip abductors and lateral ankle musculature prior to and following ground contact in an effort to decrease plantar pressure on the lateral column of the foot during the stance phase of gait. One aspect provided by an embodiment of the present invention gait training device (and related method) is able to decrease plantar pressure on the lateral column of the foot and alter muscle activity during treadmill walking in chronic ankle instability (CAI) patients or other patients, as well as users and participants. For example, an embodiment of the gait training device is able to decrease plantar pressure on the lateral column of the foot and increase peroneus longus and gluteus medius muscle activity as may be measured by surface electromyography (sEMG) (or other types of sensors, detectors or recorders) prior to and following ground contact.

An aspect of an embodiment of the present invention provides, among other things, a gait device for rehabilitating or developing a subject's lower extremity. The device may comprise: a movable belt configured for the subject to ambulate thereon; a track disposed above the movable belt generally aligned with the movable belt; and a coupler that is configured to travel along the track and attach to the distal portion of the lower extremity of the subject while the subject is ambulating on the movable belt.

An aspect of an embodiment of the present invention provides, among other things, a gait device for rehabilitating or developing a subject's lower extremity. The device may comprise: a movable belt configured for the subject to ambulate thereon; a track disposed above the movable belt generally aligned with the movable belt; a coupler that is configured to travel along the track and attach to the distal portion of the lower extremity of the subject while the subject is ambulating on the movable belt. Moreover, referring to FIGS. 3, 4 and 8, the distal portion of the lower extremity includes two ankles of the subject, lower portion of the two legs of the subject, and two feet of the subject. Further, the track is positioned to be located between the two ankles, between the lower portion of the two legs, or between the two feet. Still referring to FIGS. 3, 4 and 8, the coupler is configured to apply a medial force to the distal portion of the lower extremity during the ambulation to strengthen the ankle, knee and/or hip musculature of the subject. The medial force, for example, is represented by the arrow, MF.

An aspect of an embodiment of the present invention provides, among other things, a method for rehabilitating or developing a gait of a subject's lower extremity. The method may comprise: ambulating a subject on a movable belt; aligning a track with and above the movable belt; and coupling the distal portion of the lower extremity of the subject to the track while the subject is ambulating on the movable belt and while the coupling activity travels along the track.

An aspect of an embodiment of the present invention provides, among other things, a method for rehabilitating or developing a gait of a subject's lower extremity. The method may comprise: ambulating a subject on a movable belt; aligning a track with and above the movable belt; and coupling the distal portion of the lower extremity of the subject to the track while the subject is ambulating on the movable belt and while the coupling activity travels along the track. Moreover, referring to FIGS. 3, 4 and 8, the the distal portion of the lower extremity includes two ankles of the subject, lower portion of the two legs of the subject, and two feet of the subject. Further, the track is positioned to be located between the two ankles, between the lower portion of the two legs, or between the two feet. Still referring to FIGS. 3, 4 and 8, the coupler is configured to apply a medial force to the distal portion of the lower extremity during the ambulation to strengthen the ankle, knee and/or hip musculature of the subject. The medial force, for example, is represented by the arrow, MF.

An aspect of various embodiments of the present invention may provide a number of advantages, such as but not limited thereto, the following:

Improves gait mechanics through functional exercises.
Rehabilitates while doing cardiovascular and musculo-skeletal endurance training.
Differing resistance of bands means that rehabilitation can be personalized and progressive.

An aspect of an embodiment of the present invention provides, among other things, a gait re-trainer system and method for lower extremity pathology.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings The accompanying drawings, which are incorporated into and form a part of the instant specification, illustrate several aspects and embodiments of the present invention and, together with the description herein, serve to explain the principles of the invention.

The drawings are provided only for the purpose of illustrating select embodiments of the invention and are not to be construed as limiting the invention.

Table 1 provides the subject Demographics (n=10) of the present inventors' study.

Table 2 provides from the study the plantar pressure measures for the total foot and nine regions of the foot during treadmill walking during baseline and gait trainer conditions.

Table 3 provides from the study the surface EMG root mean square area (mV) 200 ms pre- and post-initial contact during baseline and gait trainer conditions.

DETAILED DESCRIPTION OF EXEMPLARY EMBODIMENTS OF THE PRESENT INVENTION

An aspect of an embodiment of the present invention provides, but not limited thereto, a prophylactic and rehabilitative gait re-training device and related method. The gait re-training device (and related method) is intended to use with any motorized treadmill, movable (non-motorized) treadmill or the like. While an individual walks, jogs, or runs on a treadmill, the gait re-training device will apply a medial force via elastic bands to each lower extremity, independently. The elastic bands will slide along two independent tracks of the gait re-training device. The elastic bands have varying degrees of resistance that range from low to high levels of resistance. The independent tracks are located between the legs of the individual, while the individual is on the motorized belt of the treadmill. The independent tracks span the complete anterior-posterior length of motorized treadmill belt. The medial force applied via varying degrees of elastic band resistance is intended to strengthen the ankle, knee and hip musculature in a functional manner during walking, jogging, or running on the treadmill. Medial force includes the force directed toward the great toe ("big toe") of the foot, i.e., force toward midline. Specifically, the gait re-training device is targeting the lateral ankle and lateral hip musculature.

Figure 8:
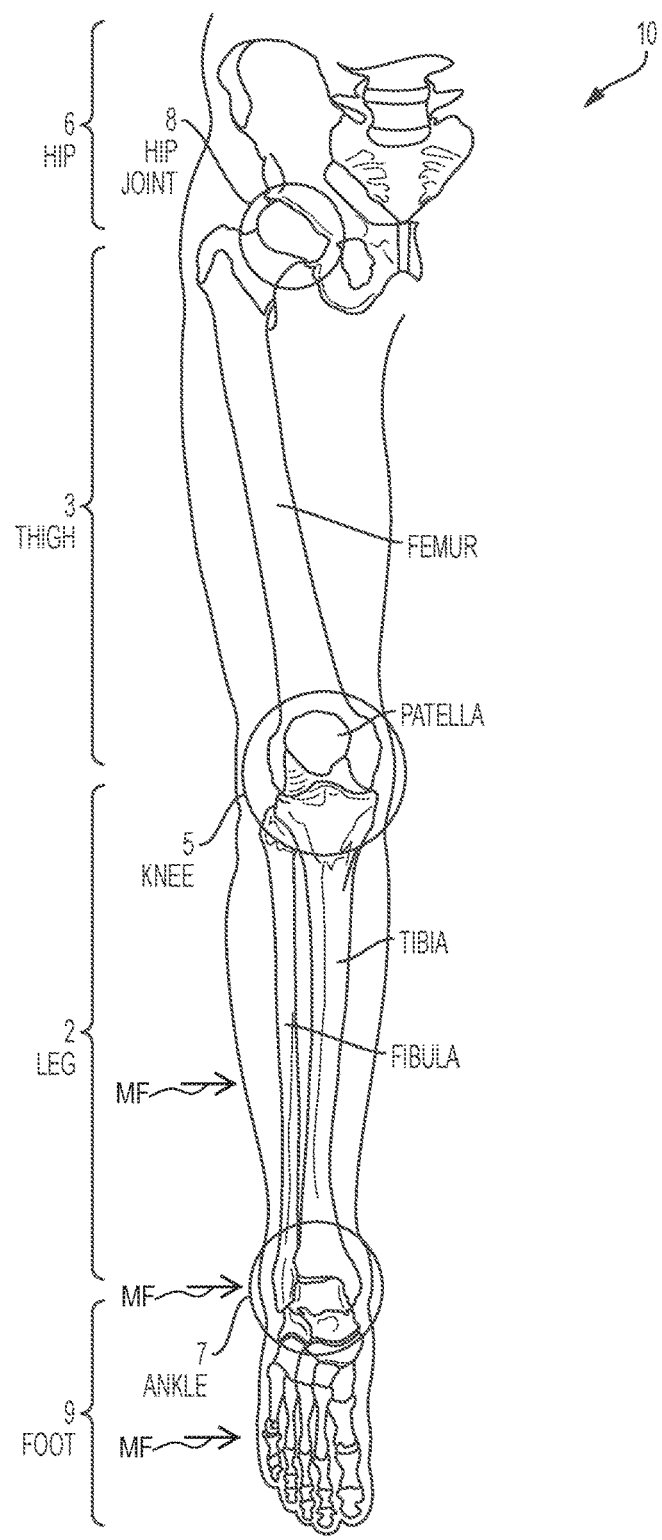
FIG. 8 provides a schematic illustration of the lower extremity, which is considered to be inclusive of the following analogous terms: lower limb, lower member; inferior member or inferior limb. The lower extremity includes: hip, hip joint, thigh, knee, leg, ankle and foot.

FIGS. 1-5 provide a schematic illustration of an embodiment of the gait device 11. FIG. 8 provides an anatomical schematic illustration of the lower extremity 10 (e.g. lower limb or inferior limb). Referring generally to FIGS. 1-5 and 8, a subject 1 is ambulating on the movable belt 15 (which may be a motorized movable belt or motorized treadmill, for example). The device 1 includes a track that may be include a first track 31 and second track 32 generally disposed above the movable belt 15 and generally aligned with said movable belt 15. The device 11 may further include a coupler that may include a first band 21 and a second band 22, and configured to travel along each track 31 and 32, respectively. The coupler (such as bands 21 and 22) is configured to attach to the distal portion of the lower extremity of the subject 1 while the subject 1 is ambulating on the movable belt 15. As illustrated, the distal portion of the lower extremity is the ankle 7 of the subject 1. Distal portion may include the leg 2, ankle 7 and the foot 9 (anything distal towards the foot or including the foot). With regards to the distal segment that the bands 21 and 22 attach to or go around the subject, the distal portion is referring to the lower part of the leg 2, just above (proximal) to the ankle 7. The bands may be attached to or go around a variety of locations or areas of the subject, including but not limited to, the foot or shoe, for example. The ambulatory motion may include walking, jogging, or running, etc. While a subject 1 walks, jogs, or runs on the movable belt 15 of the gait device 11, the gait device 11 will apply a medial force via bands 21, 22 (i.e., coupler—such as elastic bands or the like) that are coupled to each lower extremity (e.g., ankle 7), independently. The elastic bands 21, 22 will slide or translate along two independent tracks (or elongated member(s) or the like) 31 and 32 of the gait device 11. In an embodiment, the elastic bands 21, 22 have varying degrees of resistance that range from low to high levels of resistance (and any level there between). The independent tracks 31, 32 are located between the legs 2 or ankles 7 of the subject 1, while the subject 1 is on the movable belt 15 of the device 11. In an embodiment, the independent tracks 31, 32 span the complete anterior-posterior length of movable belt 15, but may have a length less than or greater than the anterior-posterior length of movable belt 15. The medial force applied via varying degrees of elastic band resistance is intended to strengthen the ankle, knee and/or hip musculature in a functional manner during walking, jogging, or running on the moveable belt 15 (e.g., treadmill). Medial force includes the force directed toward the great toe ("big toe") of the foot, i.e., force toward midline. In an embodiment, the gait device is targeting the lateral ankle and lateral hip musculature. The track(s) and coupler may be aligned with and in communication with the subject in a variety of locations or regions as desired or required. The coupler can be any connection or fastening means or mechanism that is capable of traveling along or with the track(s) as well as to connect or fasten to the subject.

In an embodiment, the first band 21 and a second band 22, of the coupler may be attached to each track 31 and 32, respectively, using connectors 23, 24. Various fastening or securing devices or mechanisms to the track may be implemented to achieve the function.

In an embodiment, a frame 35 may be provided to position and secure the track(s) 31 and 32 (as well as securing and positioning other related and required components, systems, or devices).

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient/subject or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

A module 40 may be provided that may be a variety of controllers, processors, computer or user interface. For example, the module 40 may control aspects of the gait device 11 or be in communication with sensors, detectors, systems, processors, other controllers, or other components associated with the gait device 11. The module 40 may be in communication with other local and/or remote systems, processors, computers, and devices (as well as users). The communication to and from the module 40 may be hard wired and/or wireless. Examples of the module 40 may be a machine that can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice.

The present inventors recognize that many acute and chronic lower extremity musculoskeletal injuries are a result of improper lower extremity mechanics during athletic maneuvers (running, jumping, cutting, etc.). Many athletic trainers, physical therapists, physiotherapists, physicians, chiropractors, coaches, and athletes employ various methods of prophylactic and rehabilitative exercise to improve lower extremity mechanics as a means of preventing injury and during the recovery from previous acute and chronic injuries. Of key interest in injury prevention and rehabilitation for lower extremity injuries are the muscles of the ankle, knee and hip that are responsible for frontal plane joint alignment and stability. Due to the specificities of the joint articulations (ankle, knee, and hip), only the ankle and hip have muscles capable of improving frontal plane alignment of the entire lower extremity, which may improve joint stability or alignment. Currently, the methods employed to train the ankle and hip frontal plane stabilizing muscles include non-functional exercises such as 4-way ankle strengthening for the ankle and clamshell or monster walk exercises for the hip. However, an aspect of an embodiment of the present invention provides gait re-training device targets the frontal plane stabilizing exercises during walking, jogging, and running on a motorized treadmill. The frontal plane is also known as side-to-side or coronal plane.

The unique benefits of the gait re-training device (and related method) include the ability to improve gait mechanics through functional gait re-training as compared to non-functional means currently employed in sports medicine rehabilitation applications. Furthermore, the unique application allows individuals to utilize an embodiment of the present invention gait re-training device while getting the added benefit of walking, jogging, or running, such as, cardiovascular and musculoskeletal endurance training. Lastly, rehabilitation clinicians typically utilize a progression from non-functional to functional exercises during the rehabilitation process for any injury However, up to this point, the present inventors recognize that there is a gap in the functional progression for frontal plane ankle and hip stabilizing musculature, as there is not a current method to specifically train these muscles during functional exercises. The frontal plane ankle musculature includes, for example, the motion of the ankle rolling in and out. The hip stabilizing musculature includes, for example, the muscle contraction that occurs on the outside of the hip in response to the medial force applied by the coupler (e.g., bands).

An aspect of various embodiments of the present invention may be utilized for a number of products and services. For example, potential commercial applications include any individual or group of individuals with an interest in injury prevention, rehabilitation or performance enhancement as it relates to the lower extremity. Athletic trainers, physical therapists, sports medicine physicians, or chiropractors that prescribe rehabilitation exercises for acute and chronic injuries would benefit from the functional gait re-training device. Additionally, many of these clinicians are involved in preventative medicine and would benefit from prophylactic applications of the gait re-training device. Coaches and athletes of all levels who have an interest in prevention of acute and chronic injuries would benefit from the novel gait re-training device. There is also a potential market among strength and conditioning coaches, personal trainers, and others in the fitness industry. Lastly, the department of defense may have an interest in the gait re-training device due to large number of acute and chronic injuries during training of military recruits.

In an embodiment, the gait device may be capable of performing a quantitative and diagnostic analysis of subject's movements based on the measurement of subject's stride or gait, for example. The information and data regarding the movement, stride, or gait may be obtained using a variety detectors or sensors such as, but not limited thereto, accelerometers, cameras, gyroscopes, goniometers, electromyography (EMG), and surface electromyography (sEMG). An EMG or sEMG (or other sensor or detector) may be mounted to or disposed in communication with a variety of locations on the subject or in some cases near the subject, on the device, near the device, or in communication with the device. An EMG or sEMG (or other sensor or detector) may be mounted on the clothing, shoes, glasses, hat or other apparel, garments or equipment.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

EXAMPLES

Practice of an aspect of an embodiment (or embodiments) of the invention will be still more fully understood from the following examples and experimental results, which are presented herein for illustration only and should not be construed as limiting the invention in any way.

Example and Experimental Results Set No. 1

The present inventors recently demonstrated that 4 weeks of comprehensive rehabilitation for CAI was successful at improving self-reported function, range of motion (ROM), strength, and balance but had no meaningful effect on frontal plane gait mechanics. In an attempt to specifically target gait impairments with CAI, the present inventors developed a novel gait training device. The device was designed for use with a treadmill and was developed to target activation of the hip abductors and lateral ankle musculature prior to and following ground contact in an effort to decrease plantar pressure on the lateral column of the foot during the stance phase of gait. Prior to implementing this device in a gait training rehabilitation program, its ability to alter plantar pressure and muscle activity in CAI patients must be evaluated. The present inventors' purpose was to determine if the gait training device could decrease plantar pressure on the lateral column of the foot and alter muscle activity during treadmill walking in CAI patients. The present inventors hypothesized that the gait training device would decrease plantar pressure on the lateral column of the foot and increase peroneus longus and gluteus medius muscle activity as measured by surface electromyography (sEMG) prior to and following ground contact.

Methods:
Participants

A descriptive laboratory study was performed to compare measures of plantar pressure and sEMG during treadmill walking with and without a gait training device in ten young adults with CAI. The inclusion criteria for CAI was a history of more than one ankle sprain with the initial sprain occurring greater than one year prior to study onset and no history of ankle sprain within 6 weeks of data collection. Subjects also had to have current self reported functional deficits due to ankle symptoms that was quantified by a score of <85% on the Foot and Ankle Ability (FAAM) Sport scale and a score ≥10 on the Identification of Functional Instability scale (IdFAI) (See Table 1). All participants were physically active (at least 20 minutes of exercise per day at least 3 days per week) and have no other lower extremity injuries or pathologies that would affect outcome measures. Only the subject's involved limb was utilized for data collection and analysis and in the case of bilateral CAI the subject's perceived worse limb was analyzed as the involved limb. This study was approved by the Institutional Review Board for Health Sciences Research and all subjects provided informed consent prior to participation.

TABLE 1

SUBJECT DEMOGRAPHICS (n = 10).

| | MEAN (SD) |
|---|---|
| Age (years) | 21.5 (3.1) |
| Sex | MALE: 3, FEMALE: 7 |
| Height (centimeters) | 166.0 (6.3) |
| Mass (kilograms) | 65.6 (10.4) |
| GODIN LEISURE-TIME EXERCISE QUESTIONNAIRE SCORE | 73.9 (24.5) |
| FAAM ADL % | 86.3 (7.8) |
| FAAM SPORT % | 68.1 (15.0) |
| IdFAI | 22.92 (1.71) |
| NUMBER OF ANKLE SPRAINS | 4.8 (3.2) |
| TIME SINCE LAST SPRAIN (MONTHS) | 11.5 (9.3) |

FAAM = FOOT AND ANKLE ABILITY MEASURE
ADL = ACTIVITIES OF DAILY LIVING
IdFAI = IDENTIFICATION OF FUNCTIONAL ANKLE INSTABILITY

Instruments
Plantar Pressure

Plantar pressure was measured using the Pedar-x plantar pressure system (Novel Inc, St Paul Minn., USA) with in-shoe insoles that had a sampling rate of 100 Hz. Participants used a standard athletic shoe for both conditions (Brooks Defyance 3, Brooks Sports Inc., Seattle, Wash., USA). All trials were completed on a standard laboratory treadmill (Gait Trainer™ 3, Biodex, Shirley, N.Y., USA).

Surface Electromyography

Surface EMG was collected using 2 parallel bar rectangular sensors. Each bar was 1 mm wide and 1 cm long and inter-electrode distance was 1 cm. The sensors were DE 2.1 differential EMG sensors (Delsys, Boston, Mass., USA). The signal was amplified with a gain of 1000 and digitized with a 4 channel acquisition system (Bagnoli EMG system, Delsys, Boston, Mass., USA) at 1000 Hz. Input impedance was $>10^{15} \Omega/0.2$ pF with a signal to noise ratio of 1.2 uV. Data were collected with Motion Monitor software (Innovative Sports Training, Inc., Chicago, Ill.) and processed with EMGworks software (version 4.1.1, Delsys, Boston, Mass., USA). Data were filtered using a 10-500 Hz band-pass filter and smoothed using a 50-sample moving window root mean square (RMS) algorithm. Initial contact was identified with a foot switch that was placed beneath the heel of the subject's involved limb (Delysis, Boston, Mass., USA).

Procedures

Participants provided informed consent and completed a general health history questionnaire, FAAM Activity of Daily Living and Sport scale, and IdFAI questionnaire. Next, surface electrodes were placed over the midline of each muscle belly that was determined via manual palpation during a voluntary contraction. To minimize skin impedance, the skin was shaved, abraded, and then cleansed with isopropyl alcohol. Proper sensor placement was visually inspected for crosstalk by having subjects perform voluntary contractions against manual resistance. Participants were then fitted with standard lab shoes and in-shoe pressure insoles.

Participants walked on the treadmill at their self-selected walking pace. Data were not collected until subjects reported they had achieved their self-perceived normal gait pattern. At this point, the tester collected 30 seconds of baseline gait. After completing baseline data collection, the subject was set-up with the gait training device. Since this was a preliminary investigation, the present inventors did not know if the gait training device would alter plantar pressure or sEMG immediately after use, thus the order of conditions was not randomized and baseline data collection always preceded the GTR condition.

Figure 1:
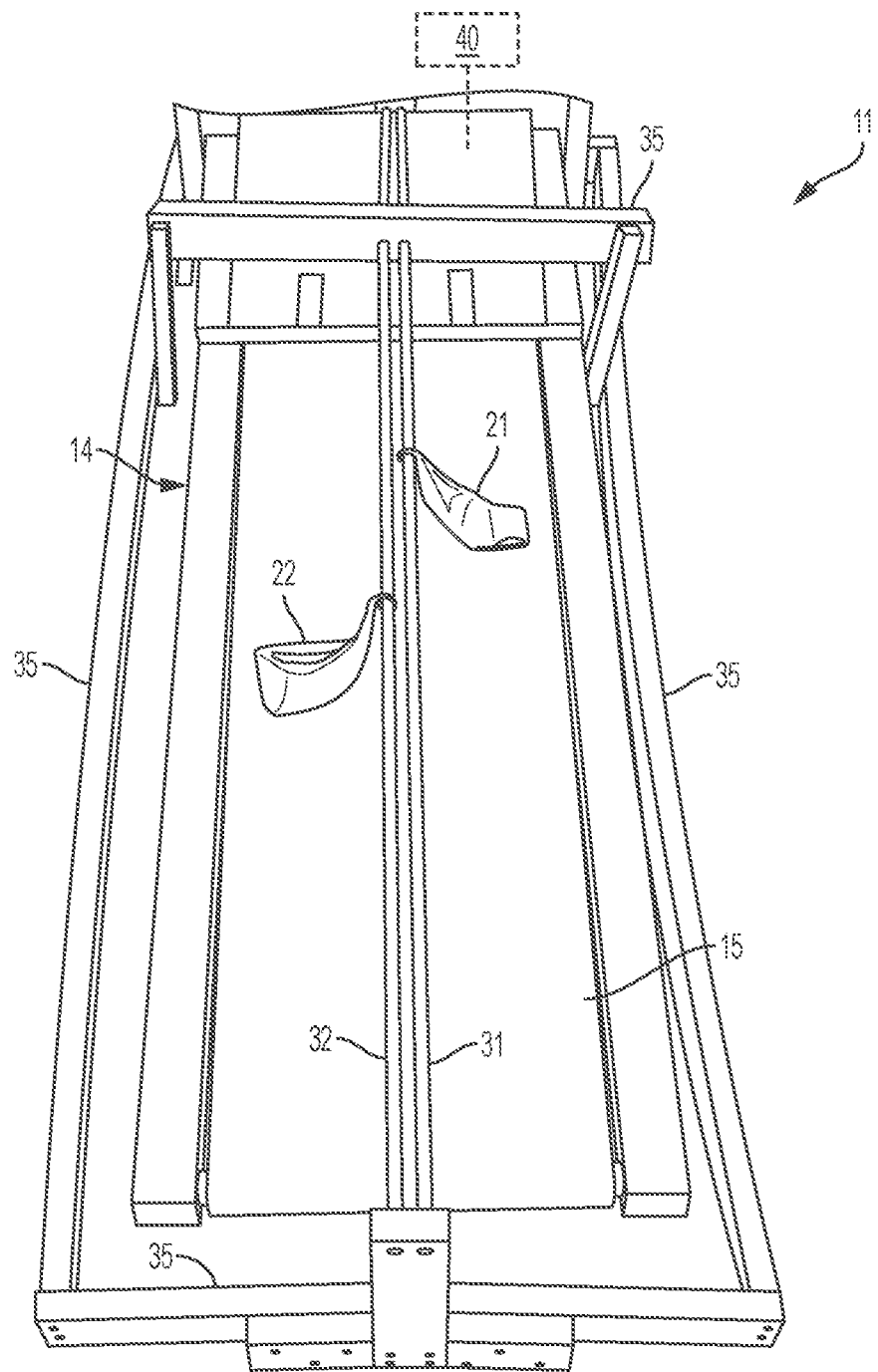
FIG. 1 provides a schematic illustration of an embodiment of the gait device.
Figure 2:
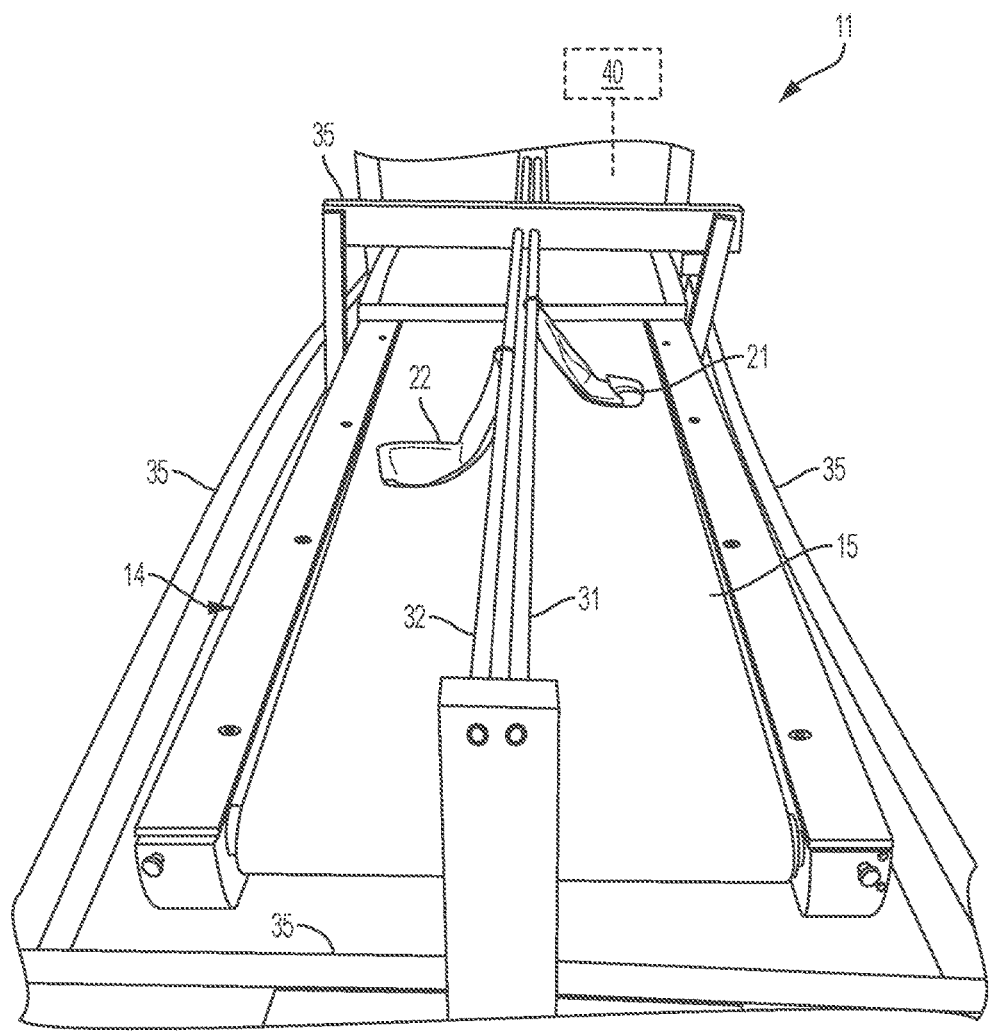
FIG. 2 provides a schematic illustration of an embodiment of the gait device.
Figure 3:
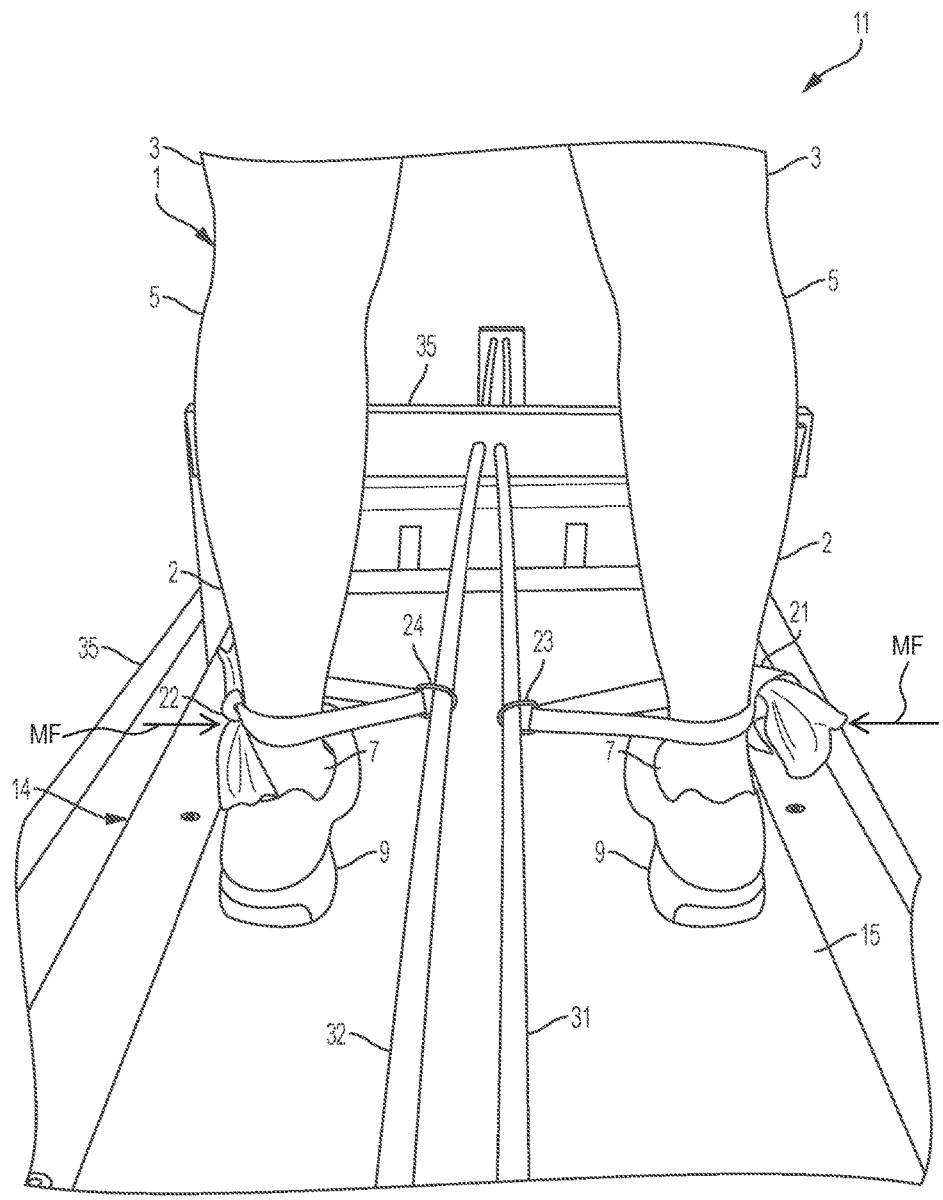
FIG. 3 provides a schematic illustration of an embodiment of the gait device having a subject standing thereon.
Figure 4:
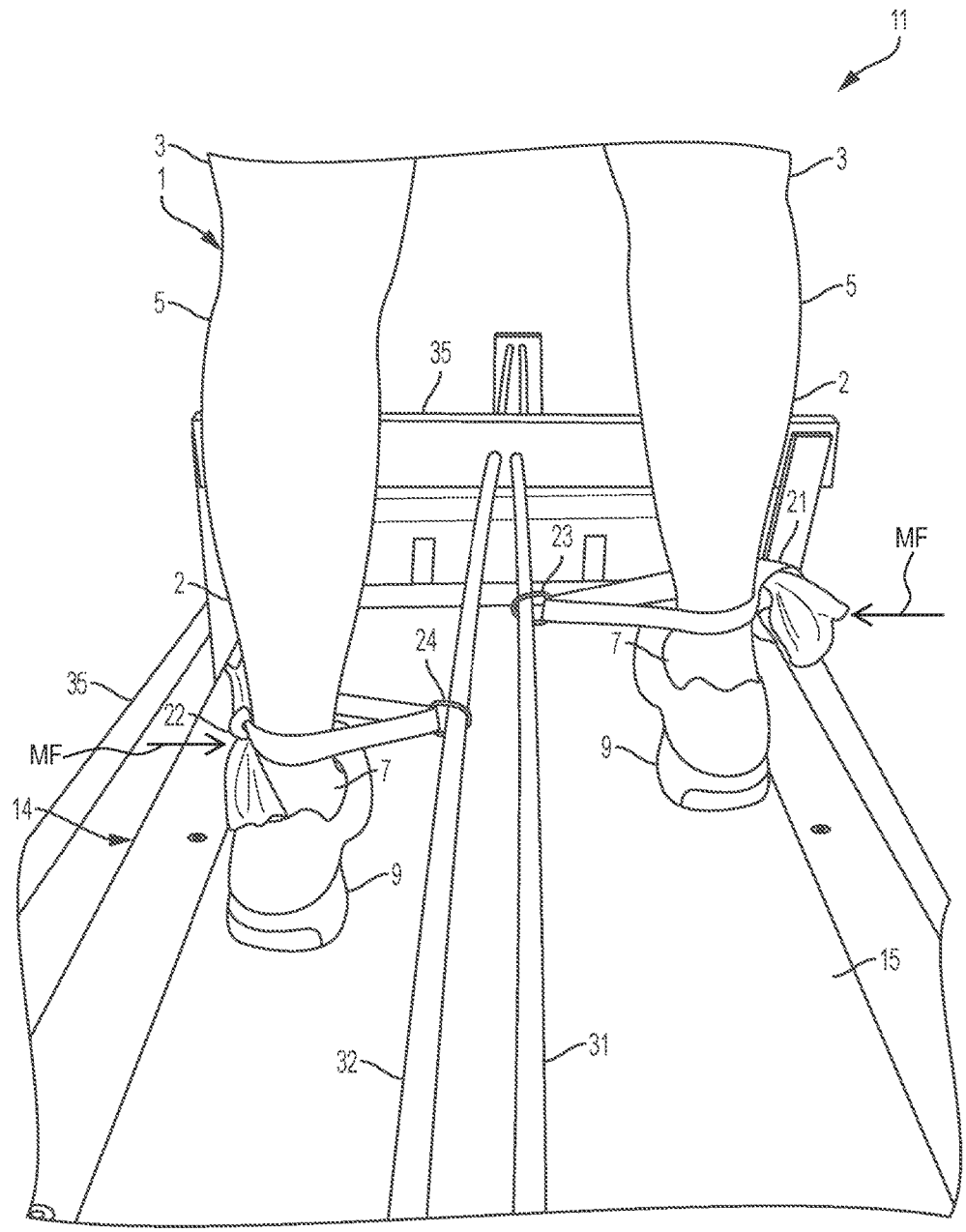
FIG. 4 provides a schematic illustration of an embodiment of the gait device having a subject walking thereon.
Figure 5:
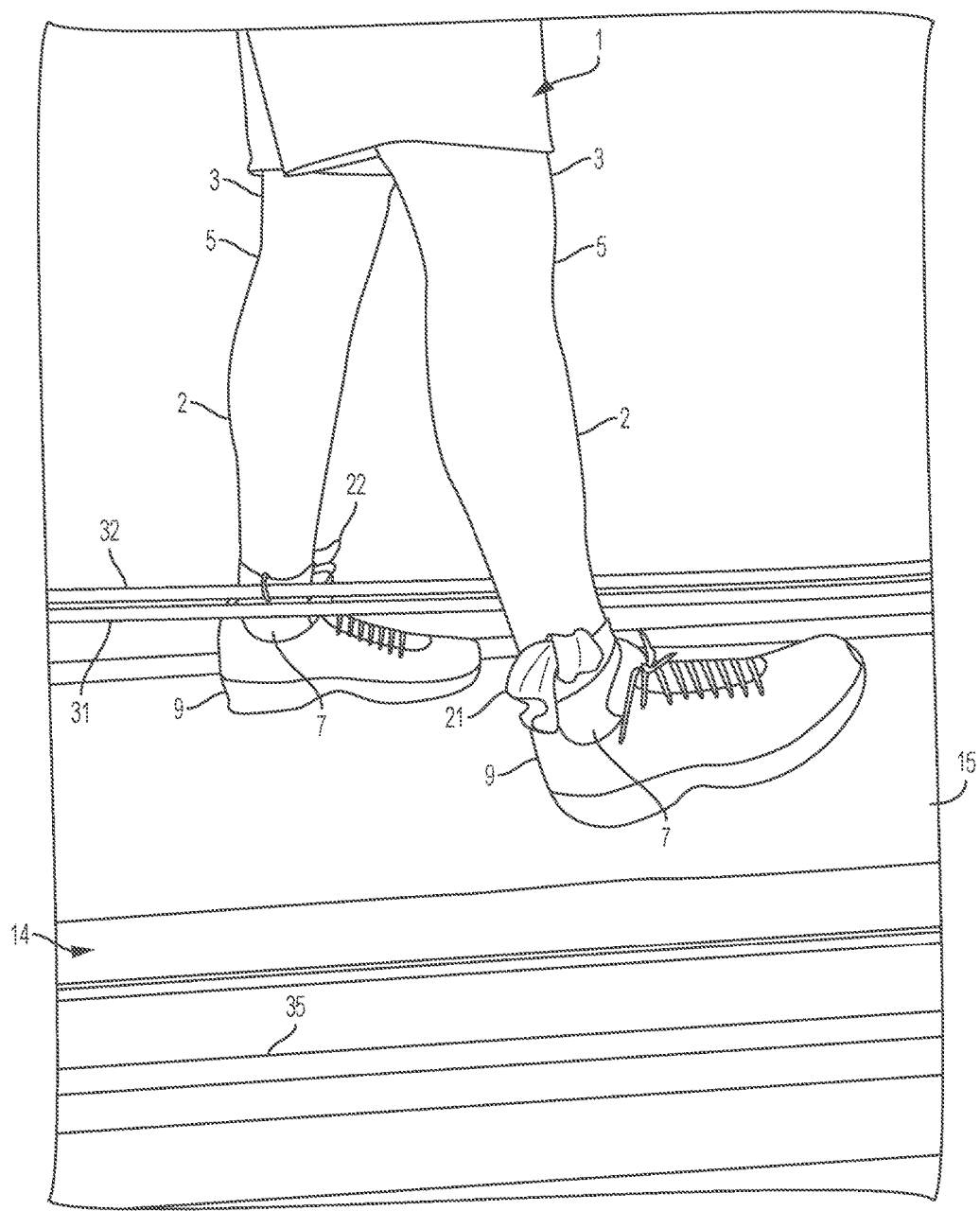
FIG. 5 provides a schematic illustration of a side view of an embodiment of the gait device having a subject walking thereon.

Participants were asked to stand with feet shoulder width apart, with the gait training device tracks positioned between their legs at a height of approximately the distal ⅓ of the participant's shank. As shown in FIGS. 3-5, for example, elastic bands were secured bilaterally around the lower leg of each participant by the tester. Elastic bands were stretched to approximately 150% of their resting length and tied around the shank. Participants then began walking at the same walking pace as baseline trials. Participants began gait training trials by holding the hand-rails of the treadmill until they accommodated to the resistance and could maintain a comfortable gait pattern. Participants were allowed to hold onto the treadmill handrails during the GTR condition, however only 2 of 10 subjects held the rails during data collection. Data were collected for GTR trials when participants felt they were comfortably walking with the resistance of the gait training device.

Data Reduction
Plantar Pressure

For peak pressure, pressure time integral, time to peak pressure, contact area and contact time the mean of 10 consecutive steps of the involved limb were processed using Novel Database Pro 1/14 and Automask software packages (Novel Inc, St Paul, Minn., USA). This was completed for the entire foot and all 9 regions of the foot (medial heel, lateral heel, medial midfoot, lateral midfoot, medial forefoot, central forefoot, lateral forefoot, hallux, and toes 2-5). Peak pressure represented the highest point of pressure in a given region of the foot during stance phase of gait. The pressure time integral was defined as the total plantar pressure applied to a specific region of the foot over the time spent in stance. Time to peak pressure was the percentage of stance when the peak pressure occurred for that specific region. Contact area and contact time indicated how large of an area and how long each region was in contact with the ground during the stance phase of gait.

Center of Pressure Gait Line

The location of the center of pressure was measured as the distance from the most medial and posterior location of each participant's involved heel. We condensed each subjects gait line into increments that represented 10% of the stance phase. Data points that represented 1-10% of stance were averaged and considered to represent the location of the center of pressure at 5% of stance. Similarly, data points that represented 11-20% of stance were averaged and considered to represent the location of the center of pressure at 15% of stance. This process was repeated for the entire stance phase. The ten resulting data points were then treated as separate dependent variables and compared between groups as described below.

Surface Electromyography

Using EMGworks software (version 4.1.1, Delsys, Boston, Mass., USA) sEMG RMS areas for the anterior tibialis, peroneus longus, medial gastrocnemius, and gluteus medius were calculated during the 200 ms prior to initial contact and during the 200 ms immediately following initial contact. The average RMS area was calculated from 10 consecutive strides for both pre- and post-initial contact sEMG epochs. The present inventors did not normalize sEMG values because all statistical comparisons were within subjects and data were collected during the same testing session without any removing of sEMG electrodes between conditions.

Statistical Analysis

Paired t-tests were used to for all dependent variables to compare baseline and GTR conditions. The level of significance set a priori at $p \leq 0.05$ for all analyses and per contemporary statistical recommendations we chose not to control for multiple comparisons. In addition to inferential statistics, Cohen's d effect sizes and associated 95% confidence intervals were also calculated to estimate the magnitude of effect during gait training trials. Effect sizes were interpreted as $\geq 0.80$ was large, 0.50-0.79 was moderate and 0.20-0.49 was small, and <0.20 was trivial. Data were analyzed using Statistical Package for Social Sciences (SPSS) Version 20.0 (SPSS, Inc, Chicago, Ill., USA).

Results:
Plantar Pressure
Pressure Time Integral (kPa*second)

Figure 7:
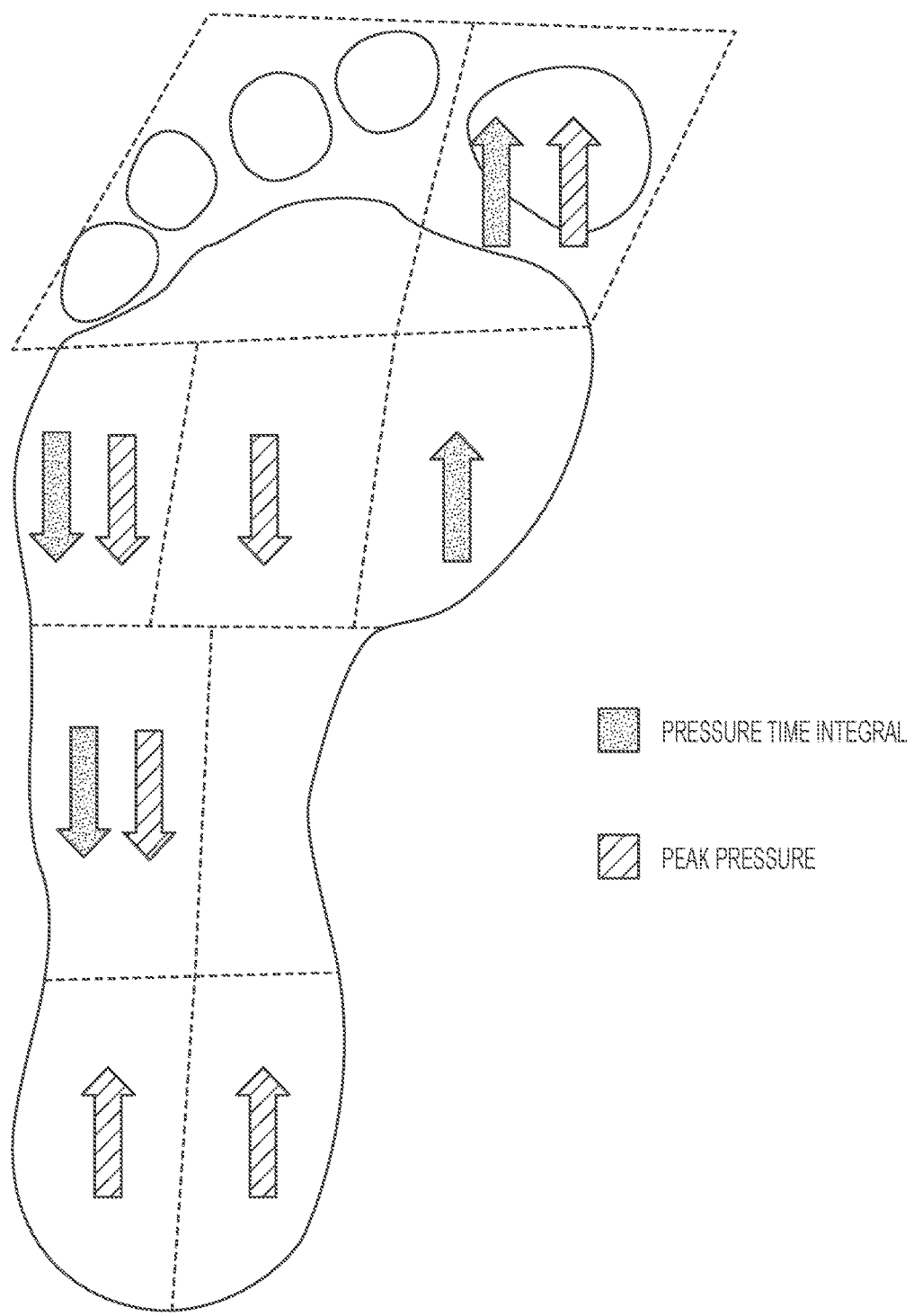
FIG. 7 schematically illustrates a summary of meaningful pressure time integral and peak plantar pressure changes during gait training trials for the nine specific regions of the foot. Total foot pressure changes are not included in figure.

There were lower pressure time integrals during GTR trials in the lateral midfoot and lateral forefoot. There were increased pressure time integrals for the total foot, medial forefoot, and hallux during the GTR condition. There were no other significant differences in pressure time integral between conditions. (Table 2 and FIG. 7)

Peak Pressure (kPa).

The GTR device significantly increased the peak pressure of the total foot, lateral heel, medial heel, and the hallux. The GTR device significantly decreased the lateral midfoot and lateral forefoot peak pressures. No other significant differences were identified for measures of peak pressure. (Table 2 and FIG. 7).

TABLE 2

PLANTAR PRESSURE MEASURED FOR THE TOTAL FOOT AND NINE REGIDNS OF THE FOOT DURING TREADMILL WALKING DURING BASELINE AND GAIT TRANER CONDITIONS.

|  |  | TOTAL FOOT | LATERAL HEEL | MEDIAL HEEL | LATERAL MIDFOOT |
|---|---|---|---|---|---|
| PRESSURE TIME INTEGRAL | BASELINE MEAN | 103.56 | 43.50 | 46.63 | 64.29 |
|  | (SD) | (17.26) | (12.51) | (10.24) | (12.13) |
| KILOPASCALS SECOND | GTR MEAN | 122.95 | 52.49 | 52.11 | 50.50 |
|  | (SD) | (25.17) | (18.42) | (15.67) | (6.48) |
|  | p-VALUE | 0.000$^a$ | 0.536 | 0.354 | 0.003$^a$ |
|  | EFFECT SIZE | 1.12 | 0.32 | 0.53 | −1.14 |
|  | (LOWER LIMIT, UPPER LIMIT) | (0.17, 2.06) | (−0.56, 1.20) | (−0.36, 1.43) | (−2.08, −0.19) |

TABLE 2-continued

PLANTAR PRESSURE MEASURED FOR THE TOTAL FOOT AND NINE REGIONS OF THE FOOT DURING TREADMILL WALKING DURING BASELINE AND GAIT TRANER CONDITIONS.

| | | | | | |
|---|---|---|---|---|---|
| PEAK PRESSURE | BASELINE MEAN | 227.70 | 145.33 | 143.46 | 129.66 |
| | (SD) | (50.88) | (14.40) | (11.29) | (25.74) |
| KILOPASCALS | GTR MEAN | 279.88 | 153.51 | 156.65 | 99.82 |
| | (SD) | (85.25) | (20.10) | (21.14) | (11.50) |
| | p-VALUE | 0.17$^a$ | 0.012$^a$ | 0.003$^a$ | 0.003$^a$ |
| | EFFECT SIZE | 1.00 | 1.26 | 2.05 | −1.16 |
| | (LOWER LIMIT, UPPER LIMIT) | (0.09, 1.96) | (0.30, 2.22) | (0.97, 3.14) | (−2.11, −0.21) |
| TIME TO PEAK PRESSURE | BASELINE MEAN | 77.89 | 17.97 | 18.11 | 54.13 |
| | (SD) | (2.89) | (4.82) | (4.68) | (15.53) |
| % OF STANCE | GTR MEAN | 74.98 | 15.61 | 15.66 | 41.05 |
| | (SD) | (12.27) | (4.34) | (4.54) | (20.53) |
| | p-VALUE | 0.405 | 0.031 | 0.078 | 0.026$^a$ |
| | EFFECT SIZE | −1.08 | −0.49 | −0.52 | −0.54 |
| | (LOWER LIMIT, UPPER LIMIT) | (−202, −0.14) | (1.38, 0.40) | (−1.41, 0.37) | (−1.76, 0.07) |
| CONTACT AREA | BASELINE MEAN | 141.02 | 18.86 | 20.33 | 23.98 |
| | (SD) | (10.87) | (1.12) | (1.30) | (1.66) |
| CENTIMETERS$^2$ | GTR MEAN | 140.89 | 18.89 | 20.23 | 23.18 |
| | (SD) | (10.72) | (0.90) | (1.35) | (1.60) |
| | p-VALUE | 0.980 | 0.813 | 0.138 | 0.020$^a$ |
| | EFFECT SIZE | −0.002 | 0.03 | −0.05 | −0.49 |
| | (LOWER LIMIT, UPPER LIMIT) | (−0.07, 0.87) | (−0.85, 0.90) | (−0.93, 0.82) | (−1.38, 0.40) |
| CONTACT TIME | BASELINE MEAN | 749.20 | 620.50 | 570.00 | 743.20 |
| | (SD) | (97.18) | (122.47) | (104.52) | (93.38) |
| MILLISECONDS | GTR MEAN | 808.80 | 625.50 | 500.40 | 787.00 |
| | (SD) | (135.51) | (242.50) | (227.48) | (120.62) |
| | p-VALUE | 0.184 | 0.952 | 0.693 | 0.273 |
| | EFFECT SIZE | 0.61 | 0.04 | 0.29 | 0.47 |
| | (LOWER LIMIT, UPPER LIMIT) | (−0.28, 1.51) | (−0.84, 0.92) | (−0.59, 1.17) | (−0.42, 1.36) |

| | | MEDIAL MIDFOOT | LATERAL FOREFOOT | CENTRAL FOREFOOT | MEDIAL FOREFOOT | TOEB2-5 | HALLUX |
|---|---|---|---|---|---|---|---|
| PRESSURE TIME INTEGRAL | BASELINE MEAN | 39.48 | 68.61 | 60.33 | 53.94 | 47.15 | 58.18 |
| | (SD) | (10.08) | (14.90) | (15.37) | (12.04) | (10.20) | (17.98) |
| KILOPASCALS SECOND | GTR MEAN | 38.15 | 58.950 | 59.81 | 61.34 | 545.51 | 80.41 |
| | (SD) | (11.92) | (13.46) | (18.26) | (16.53) | (18.07) | (26.37) |
| | p-VALUE | 0.522 | 0.023$^a$ | 0.872 | 0.045$^a$ | 0.105 | 0.005$^a$ |
| | EFFECT SIZE | −0.13 | −0.66 | −0.00 | 0.61 | 0.82 | 1.27 |
| | (LOWER LIMIT, UPPER LIMIT) | (−1.01, 0.75) | (−1.56, 0.25) | (−0.91, 0.84) | (−0.28, 1.51) | (−0.09, 1.73) | (0.28, 2.19) |
| PEAK PRESSURE | BASELINE MEAN | 87.93 | 157.60 | 173.07 | 157.91 | 148.07 | 203.23 |
| | (SD) | (15.15) | (28.00) | (23.02) | (24.39) | (19.79) | (67.25) |
| KILOPASCALS | GTR MEAN | 85.96 | 130.20 | 155.04 | 158.22 | 159.02 | 276.10 |
| | (SD) | (13.00) | (30.72) | (33.95) | (36.34) | (29.57) | (89.42) |
| | p-VALUE | 0.536 | 0.005$^a$ | 0.040$^a$ | 0.184 | 0.128 | 0.002$^a$ |
| | EFFECT SIZE | −0.13 | −0.97 | −0.78 | 0.42 | 0.56 | 1.08 |
| | (LOWER LIMIT, UPPER LIMIT) | (−1.01, 0.75) | (−1.89, −0.04) | (−1.69, 0.13) | (−0.46, 1.31) | (−0.34, 1.45) | (0.14, 2.02) |
| TIME TO PEAK PRESSURE | BASELINE MEAN | 52.01 | 73.72 | 78.26 | 77.56 | 79.97 | 82.49 |
| | (SD) | (22.27) | (9.72) | (4.53) | (4.28) | (4.32) | (2.48) |
| % OF STANCE | GTR MEAN | 45.34 | 68.85 | 75.42 | 76.09 | 79.87 | 82.83 |
| | (SD) | (22.87) | (13.48) | (5.66) | (3.05) | (4.21) | (2.86) |
| | p-VALUE | 0.327 | 0.143 | 0.109 | 0.277 | 0.959 | 0.631 |
| | EFFECT SIZE | −0.30 | −0.50 | −0.63 | −0.34 | −0.02 | 0.14 |
| | (LOWER LIMIT, UPPER LIMIT) | (−1.18, 0.58) | (1.39, 0.39) | (−1.52, 0.27) | (−1.23, 0.54) | (0.90, 0.85) | (−0.74, 1.01) |
| CONTACT AREA | BASELINE MEAN | 14.19 | 13.20 | 13.74 | 11.92 | 15.27 | 9.44 |
| | (SD) | (6.41) | (0.75) | (0.61) | (0.78) | (2.99) | (1.18) |
| CENTIMETERS$^2$ | GTR MEAN | 14.06 | 13.08 | 13.75 | 12.07 | 15.80 | 9.81 |
| | (SD) | (5.90) | (0.85) | (0.61) | (0.71) | (2.31) | (0.85) |
| | p-VALUE | 0.900 | 0.466 | 0.297 | 0.331 | 0.537 | 0.193 |
| | EFFECT SIZE | −0.02 | −0.16 | 0.02 | 0.19 | 0.18 | 0.32 |
| | (LOWER LIMIT, UPPER LIMIT) | (−0.90, 0.86) | (−1.04, 0.71) | (−0.86, 0.89) | (−0.69, 1.07) | (−0.70, 1.06) | (−0.57, 1.20) |
| CONTACT TIME | BASELINE MEAN | 693.30 | 743.23 | 672.20 | 623.70 | 648.10 | 597.00 |
| | (SD) | (95.48) | (91.66) | (114.57) | (110.18) | (101.08) | (101.64) |
| MILLISECONDS | GTR MEAN | 704.80 | 783.10 | 632.90 | 629.50 | 645.80 | 616.70 |
| | (SD) | (129.36) | (86.58) | (169.36) | (138.29) | (175.38) | (142.27) |
| | p-VALUE | 0.584 | 0.237 | 0.811 | 0.856 | 0.982 | 0.587 |
| | EFFECT SIZE | 0.12 | 0.44 | 0.09 | 0.05 | −0.02 | 0.19 |
| | (LOWER LIMIT, UPPER LIMIT) | (−0.76, 1.00) | (−0.45, 1.32) | (−0.78, 0.97) | (−0.82, 0.99) | (−0.90, 0.85) | (0.58, 1.07) |

GTR = GAIT TRAINER;
SD = STANDARD DEVIATION NEGATIVE EFFECT SIZE REPRESENTSA LOWER MEAN DURNG THE GAIT TRANER CONDITION, LOWER LIMIT AND UPPER LIMIT REPRESENT THE 95% CONFIDENCE INTERVAL FOR THE EFFECT SIZE.
$^a$INDICATES SIGNFICANT DIFFERENCE BETIME CONDITIONS ($P \leq 0.05$).

Time to Peak Pressure (% of Stance)

Time to peak pressure for the lateral midfoot occurred earlier in stance while participants were using the GTR device. No other significant differences were identified for time to peak pressure. (Table 2).

Contact Area (cm$^2$)

The lateral midfoot contact area was significantly reduced during GTR trials. There were no other significant changes in contact area. (Table 2).

Contact Time (ms)

There were no significant differences in contact time for the entire foot or for any region of the foot between conditions. (Table 2).

Center of Pressure Gait Line

Figure 6:
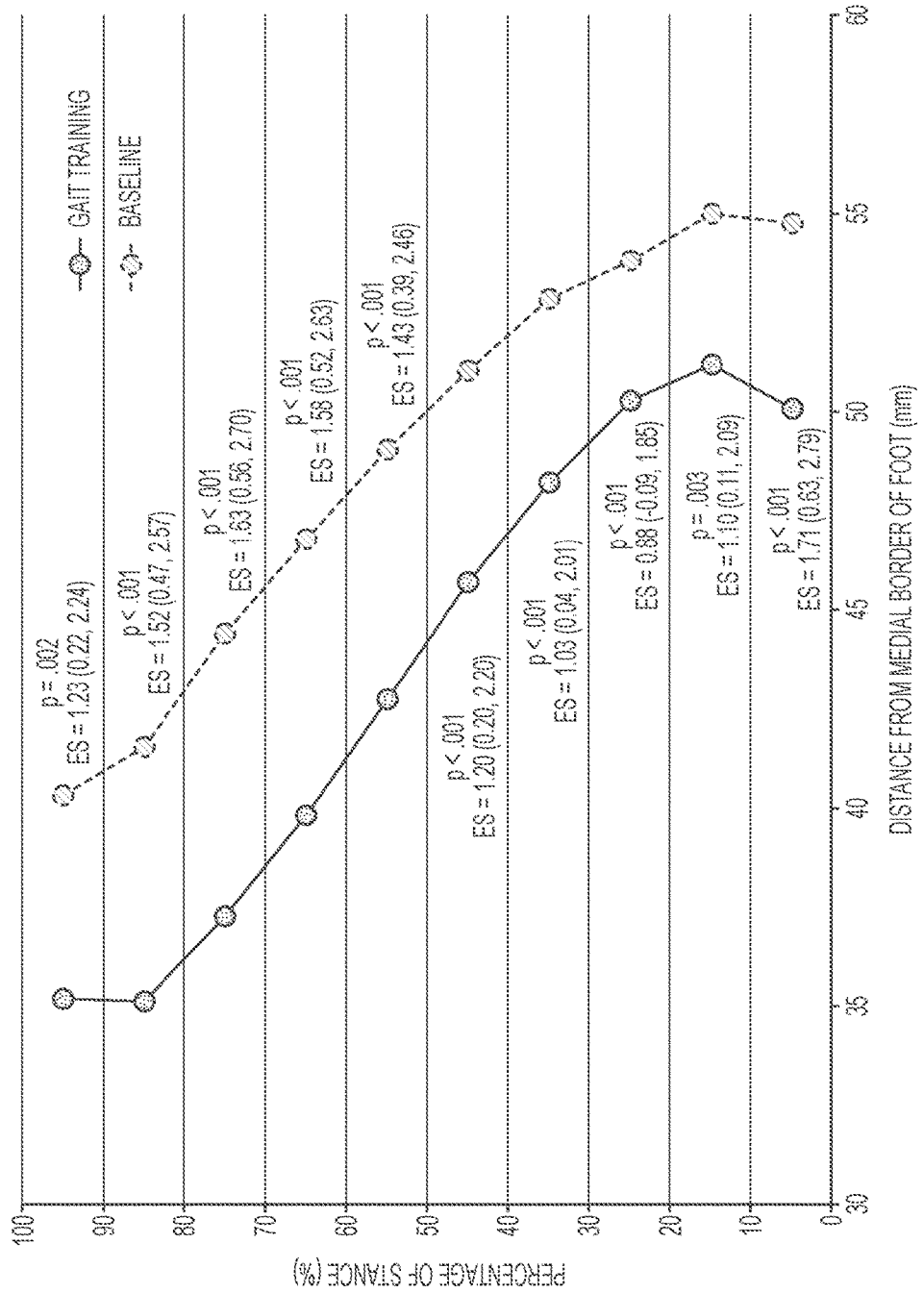
FIG. 6 graphically illustrates an average location of center of pressure during 10% increments during stance phase of gait for baseline and gait trainer conditions. Positive effect size indicates medial shift of location of center of pressure in the gait trainer condition ES=effect size, (Lower limit, Upper limit) represent the 95% confidence interval for the effect size.

The center of pressure was shifted significantly medially for all ten comparisons during the stance phase in the GTR condition (p<0.003 with large effect sizes for all comparisons). (FIG. 6).

Surface Electromyography (mV)

The GTR device significantly increased the peroneus longus muscle activity (RMS area) during the 200 ms prior to and the 200 ms following initial contact (See Table 3). There were no other significant differences in sEMG RMS areas between conditions.

and barefoot running when compared to healthy controls. The present inventors recommended that clinicians intervene in a way that would decrease the amount of rearfoot inversion at ground contact and during loading to create a more medial center of pressure trajectory. McKeon et al. demonstrated that four weeks of supervised balance training can significantly alter shank and rearfoot coupling during gait, but was ineffective at improving inversion/eversion kinematics in CAI patients. Donovan et al. subsequently demonstrated that four weeks of comprehensive rehabilitation was also ineffective at restoring normal gait and that specifically targeting gait abnormalities is likely required. It has been speculated that peroneal pre-activation is a compensatory mechanism exhibited by CAI patients to improve foot and ankle frontal plane alignment prior to ground contact. The present inventors have previously questioned whether altered use of the peroneus longus prior to initial contact could have deleterious consequences that may prevent CAI patients from adequately everting during stance and thus contribute to the increased lateral loading. The present inventors' current results suggest that large increases in peroneus longus pre-initial contact activation is capable of improving the location of the center of pressure during the first 10% of stance. Furthermore, the moderate increases in

TABLE 3

Surface EMG root mean square area (mV * sec) 200 ms pre- and post-initial contact during baseline and gait trainer conditions

| Muscles | Pre-Initial Contact Mean (SD) | | Paired T-Test p-value | Pre-Initial Contact Effect Size (Lower Limit, Upper Limit) Baseline-Gait Trainer | Pre-Initial Contact Mean (SD) | | Paired T-Test p-value | Post-Initial Contact Effect Size (Lower Limit, Upper Limit) Baseline-Gait Trainer |
|---|---|---|---|---|---|---|---|---|
| | Baseline | Gait Trainer | | | Baseline | Gait Trainer | | |
| Anterior Tibialis | 595.74 (250.49) | 830.22 (537.22) | 0.099 | 0.93 (0.01, 1.86) | 1032.62 (647.79) | 1275.23 (756.67) | 0.061 | 0.37 (−0.51, 1.26) |
| Peroneus Longus | 147.45 (61.33) | 227.64 (92.40) | 0.002* | 1.31 (0.34, 2.27) | 249.95 (156.38) | 379.05 (185.39) | 0.002* | 0.63 (−0.26, 1.53) |
| Medical Gastrocnemius | 397.27 (335.82) | 517.86 (547.27) | 0.400 | 0.38 (−0.52, 1.24) | 242.19 (181.93) | 477.67 (454.28) | 0.058 | 1.29 (0.33, 2.26) |
| Gluteus Medius | 140.59 (93.09) | 154.15 (85.29) | 0.394 | 0.15 (−0.73, 1.02) | 184.99 (135.27) | 241.06 (180.60) | 0.095 | 0.41 (−0.47, 1.30) |

SD = Standard Deviation
*Indicates significant difference between conditions (p < 0.05)
Positive effect size represents higher amplitude in the gait trainer condition, Lower limit and upper limit represent the 95% confidence interval for the effective size Discussion The gait training device was able to change the plantar pressure distribution during gait in CAI patients. The present inventors identified moderate to large decreases in the pressure time integral and peak pressure in the lateral midfoot and lateral forefoot. The decreased plantar pressure on the lateral column of the foot was accompanied by small to large increases in plantar pressure in the central forefoot, medial forefoot, and hallux. There were corresponding increases in peroneus longus muscle activity prior to and following ground contact. The present inventors' analysis of the location of the center of pressure suggests that there is a systematic shift in the center of pressure medially as all ten comparisons had large medial shifts in the location of the center of pressure. Furthermore, as indicated by FIG. 6, the gait line was more medial with the GTR device throughout all of stance, and it followed a similar pattern of progression when compared to baseline trials.

The present inventors have identified that CAI patients have increased lateral loading during walking, shod jogging, peroneus longus muscle activity following initial contact were sufficient to maintain a more medial center of pressure during all phases of stance. While the present inventors cannot be certain, they speculate that a medial shift in plantar pressure at and following initial contact may be related to a less inverted foot position prior to and following ground contact.

Previous studies have prospectively investigated the relationship between gait biomechanics and first time acute ankle sprains. In healthy individuals without a history of ankle sprain, a laterally deviated center of pressure at initial contact with subsequent excessive pronation during midstance and toe off is associated with the initial sprain. Interestingly, numerous studies have identified the same laterally deviated foot position at initial contact in CAI patients; however, CAI patients typically maintain the laterally deviated center of pressure throughout the remainder of stance. Collectively, these results suggest that the position of the foot and ankle prior to ground contact is important for first time and recurrent sprains. Additionally, the results add credence to the theory that CAI gait patterns may be an ineffective coping strategy at preventing future sprain.

To our knowledge, this is the first study to utilize a gait training device to alter the plantar pressure and muscle activity in CAI patients. Along with our hypothesized related results, we also identified increased pressure time integrals and peak pressures for the total foot. The present inventors believe the increased pressure for the total foot was a consequence of participants completing the gait cycle while being attached to elastic resistance. The relative increase from baseline trials was approximately 20% and future research that implements such rehabilitation devices for greater lengths of time should be aware of the increased total force. When using the GTR device, participants also reached peak pressure 13% earlier during stance in the lateral midfoot when compared to baseline trials, however, this is likely related to the more medial center of pressure and the significant reduction in contact time seen within that area of the foot.

The present inventors also hypothesized to identify increased gluteus medius sEMG activity prior to and following initial contact due to the medially directed force during swing and stance phases of gait. The post initial contact comparison for gluteus medius sEMG activity had a p-value of 0.095 and a small effect size, suggesting the present inventors may have been underpowered for this dependent variable. Furthermore, the anterior tibialis sEMG activity prior to and following initial contact and the medial gastrocnemius sEMG activity following initial contact all had p-values <0.10 with small to large effect sizes, further suggesting we may have been underpowered for certain sEMG comparisons.

Limitations

The present inventors acknowledge that these results were during a single intervention while CAI patients were using the device and cannot speculate on the long-term effects or utility of the GTR device in a clinical setting. Another limitation was that the order of trials was not randomized, however, we choose to collect baseline measures before using the gait training device because we did not know if gait would be altered immediately after using the device. The present inventors' small sample size may have increased the potential risk for type II error in comparisons where statistical significant was not found. Specifically, 4 of the 6 non-significant comparisons of sEMG activity between conditions had P-values <0.01 but >0.05, suggesting the potential for type II error exists for those dependent variables. Lastly, kinematic data were not concurrently collected thus the present inventors can only speculate about the relationship between plantar pressure on the lateral column of the foot and rearfoot inversion/eversion kinematics.

CONCLUSION

The GTR device was successful at decreasing plantar pressure on the lateral aspect of the foot and creating a more medial center of pressure gait line throughout stance. Medial changes in center of pressure were accompanied by concurrent increases in peroneus longus muscle activity. Preliminary results suggest future research should be performed to analyze the efficacy of implementing the GTR device to improve plantar pressure during gait in CAI patients.

ADDITIONAL EXAMPLES

Example 1

An aspect of an embodiment of the present invention provides, among other things, a gait device for rehabilitating or developing a subject's lower extremity. The device may comprise: a movable belt configured for the subject to ambulate thereon; a track disposed above the movable belt generally aligned with the movable belt; and a coupler that is configured to travel along the track and attach to the distal portion of the lower extremity of the subject while the subject is ambulating on the movable belt.

Example 2

The gait device of example 1, wherein:
said coupler is configured to apply a medial force to the distal portion of the lower extremity during the ambulation to strengthen the ankle, knee and/or hip musculature of the subject.

Example 3

The gait device of example 2, wherein:
said applied medial force is of varying degrees of force.

Example 4

The gait device of example 2 (as well as subject matter in whole or in part of example 3), wherein said distal portion of the lower extremity includes an ankle of the subject, lower portion of the leg of the subject, or foot of the subject.

Example 5

The gait device of example 1 (as well as subject matter of one or more of any combination of examples 2-4, in whole or in part), wherein said movable belt is motorized.

Example 6

The gait device of example 1 (as well as subject matter of one or more of any combination of examples 2-5, in whole or in part), further comprising a sensor to determine movement of the subject.

Example 7

The gait device of example 6 (as well as subject matter of one or more of any combination of examples 2-6, in whole or in part), wherein said sensor is disposed on the subject, apparel of the subject, and/or said gait device.

Example 8

The gait device of example 6 (as well as subject matter of one or more of any combination of examples 2-7, in whole or in part), further comprising a processor or computer.

Example 9

The gait device of example 1 (as well as subject matter of one or more of any combination of examples 2-8, in whole or in part), further comprising a processor or computer.

Example 10

An aspect of an embodiment of the present invention provides, among other things, a method for rehabilitating or developing a gait of a subject's lower extremity. The method may comprise: ambulating a subject on a movable belt; aligning a track with and above the movable belt; and coupling the distal portion of the lower extremity of the subject to the track while the subject is ambulating on the movable belt and while the coupling activity travels along the track.

Example 11

The method of example 1, further comprising:
applying a medial force to the distal portion of the lower extremity during the ambulation to strengthen the ankle, knee and/or hip musculature of the subject.

Example 12

The method of example 11, further comprising: varying the degree of the applied medial force.

Example 13

The method of example 11 (as well as subject matter in whole or in part of example 12), wherein said distal portion of the lower extremity includes an ankle of the subject, lower portion of the leg of the subject, or foot of the subject.

Example 14

The method of using any of the devices or its components provided in any one or more of examples 1-9.

Example 15

The method of manufacturing any of the devices or its components provided in any one or more of examples 1-9.

Example 16

A non-transitory machine readable medium including instructions for rehabilitating or developing a gait of a subject's lower extremity, which when executed by a machine (e.g. processor), cause the machine (e.g., processor) to perform any of the steps or activities provided in any one or more of examples 1-13.

REFERENCES

The devices, systems, materials, compositions, components, sub-components, electronics, circuitry, processors, computer program products, non-transitory computer readable medium, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

1. U.S. Patent Application Publication No. US 2004/0192511 A1, Ein-Gal, M., "Treadmill", Sep. 30, 2004.
2. U.S. Patent Application Publication No. US 2008/0070757 A1, Albert, T., "Device for the Reeducation of Motory Deficiencies, Particularly Deficiencies when Walking, in Patients", Mar. 20, 2008.
3. U.S. Pat. No. 9,186,552 B1, Deal, T., "Multiuse Treadmill Apparatus", Nov. 17, 2015.
4. U.S. Pat. No. 7,455,620 B2, Frykman, P., et al., "Method for Interpreting Forces and Torques Exerted by a Left and Right Foot on a Dual-Plate Treadmill", Nov. 25, 2008.
5. U.S. Patent Application Publication No. US 2010/0035727 A1, Brunner, W., "Gait Analysis Apparatus and Method Using a Treadmill", Feb. 11, 2010.
6. U.S. Pat. No. 8,628,485 B2, Wilson, R., et al., "Gait Analysis System and Methods", Jan. 14, 2014.
7. U.S. Patent Application Publication No. US 2013/0324888 A1, Solinsky, J., "System and Method for Measuring Balance and Track Motion in Mammals", Dec. 5, 2013.
8. U.S. Patent Application Publication No. US 2010/0152629 A1, Haas, Jr., et al., "Integrated System to Assist in the Rehabilitation and/or Exercising of a Single Leg After Stroke or Other Unilateral Injury", Jun. 17, 2010.
9. U.S. Pat. No. 9,084,712 B2, Roerdink, M., et al., "Device and Method for Displaying Target Indications for Foot Movements to Persons with a Walking Disorder", Jul. 21, 2015.
10. U.S. Pat. No. 8,308,618 B2, Bayerlein, D., et al., "Treadmill with Integrated Walking Rehabilitation Device", Nov. 13, 2012.
11. U.S. Pat. No. 8,920,347 B2, Bayerlein, D., et al., "Treadmill with Integrated Walking Rehabilitation Device", Dec. 30, 2014.
12. U.S. Patent Application Publication No. US 2008/0234113 A1, Einav, O., "Gait Rehabilitation Methods and Apparatuses", Sep. 25, 2008.
13. U.S. Patent Application Publication No. US 2016/0074272 A1, Ahn, S., et al., "Method and Apparatus for Recognizing Gait Task", Mar. 17, 2016.
14. Waterman B R, Owens B D, Davey S, Zacchilli M A, Belmont P J. The epidemiology of ankle sprains in the united states. Journal of Bone & Joint Surgery, American Volume. 2010; 92-A(13):2279-2284.
15. Gerber J P, Williams G N, Scoville C R, Arciero R A, Taylor D C. Persistent disability associated with ankle sprains: A prospective examination of an athletic population. Foot & Ankle International. 1998; 19(10):653-660.
16. van Rijn R M, van Os A G, Bernsen R M, Luijsterburg P A, Koes B W, Bierma-Zeinstra S M. What is the clinical course of acute ankle sprains? A systematic literature review. Am J Med. 2008; 121(4):324-331.
17. Verhagen R, De Keizer G, Van Dijk C. Long-term follow-up of inversion trauma of the ankle. Arch Orthop Trauma Surg. 1995; 114(2):92-96.
18. Gribble P A, Delahunt E, Bleakley C, et al. Selection criteria for patients with chronic ankle instability in controlled research: A position statement of the international ankle consortium. journal of orthopaedic & sports physical therapy. 2013; 43(8):585-591.
19. Hertel J. Sensorimotor deficits with ankle sprains and chronic ankle instability. Clin Sports Med. 2008; 27(3): 353-370.
20. Hiller C E, Nightingale E J, Lin C W, Coughlan G F, Caulfield B, Delahunt E. Characteristics of people with recurrent ankle sprains: A systematic review with meta-analysis. Br J Sports Med. 2011; 45(8):660-672.
21. Donovan L, Hertel J. A new paradigm for rehabilitation of patients with chronic ankle instability. The Physician and sportsmedicine. 2012; 40(4):41-51.
22. Hoch M C, McKeon P O. Joint mobilization improves spatiotemporal postural control and range of motion in those with chronic ankle instability. Journal of Orthopaedic Research. 2011; 29(3):326-332.
23. Vicenzino B, Branjerdporn M, Teys P, Jordan K. Initial changes in posterior talar glide and dorsiflexion of the ankle after mobilization with movement in individuals with recurrent ankle sprain. Journal of Orthopaedic & Sports Physical Therapy. 2006; 36(7):464-471.
24. Terada M, Pietrosimone B G, Gribble P A. Therapeutic interventions for increasing ankle dorsiflexion after ankle sprain: A systematic review. Journal of athletic training. 2013; 48(5):696-709.
25. Arnold B L, Linens S W, Motte d I, Ross S E. Concentric evertor strength differences and functional ankle instability: A meta-analysis. Journal of Athletic Training. 2009; 44(6):653-662.
26. Holmes A, Delahunt E. Treatment of common deficits associated with chronic ankle instability. Sports Medicine. 2009; 39(3):207-224.
27. Docherty C L, Moore J H, Arnold B L. Effects of strength training on strength development and joint position sense in functionally unstable ankles. J Athl Train. 1998; 33(4):310-314.
28. Sekir U, Yildiz Y, Hazneci B, Ors F, Aydin T. Effect of isokinetic training on strength, functionality and proprioception in athletes with functional ankle instability. Knee surgery, sports traumatology, arthroscopy. 2007; 15(5): 654-664.
29. Mckeon P, Ingersoll C, Kerrigan D C, Saliba E, Bennett B, Hertel J. Balance training improves function and postural control in those with chronic ankle instability. Medicine Science in Sports Exercise. 2008; 40(10):1810.
30. Delahunt E, Monaghan K, Caulfield B. Altered neuromuscular control and ankle joint kinematics during walking in subjects with functional instability of the ankle joint. Am J Sports Med. 2006; 34(12):1970-1976.
31. Drewes L K, McKeon P O, Paolini G, et al. Altered ankle kinematics and shank-rear-foot coupling in those with chronic ankle instability. J Sport Rehab. 2009; 18(3):375-388.
32. Feger M, Donovan L, Hart J, Hertel J. Lower extremity muscle activation in patients with and without chronic ankle instability. Journal of Athletic Training. IN PRESS.
33. Morrison K E, Hudson D J, Davis I S, et al. Plantar pressure during running in subjects with chronic ankle instability. Foot & ankle international/American Orthopaedic Foot and Ankle Society [and] Swiss Foot and Ankle Society. 2010; 31(11):994.
34. Ty Hopkins J, Coglianese M, Glasgow P, Reese S, Seeley M K. Alterations in evertor/invertor muscle activation and center of pressure trajectory in participants with functional ankle instability. Journal of Electromyography & Kinesiology. 2012; 22(2):280-285.
35. Schmidt H, Sauer L D, Sae Y L, Saliba S, Hertel J. Increased in-shoe lateral plantar pressures with chronic ankle instability. Foot & Ankle International. 2011; 32(11):1075-1080.
36. Nawata K K. Plantar pressure distribution during gait in athletes with functional instability of the ankle joint: Preliminary report. Journal of orthopaedic science: official journal of the Japanese Orthopaedic Association. 2005; 10(3):298-301.
37. Koldenhoven R M, Feger M A, Fraser J J, Saliba S, Hertel J. Surface electromyography and plantar pressure during walking in young adults with chronic ankle instability. Knee Surgery, Sports Traumatology, Arthroscopy. 2016:1-11.
38. Donovan L, Hart J M, Saliba S, et al. Effect of ankle destabilization device and rehabilitation on gait biomechanics in chronic ankle instability patients: A randomized controlled trial. Physical Therapy in Sport. 2016; IN PRESS.
39. Donovan L, Hart J, Saliba S, et al. Rehabilitation for chronic ankle instability with and without destabilization devices: A randomized controlled trial. J Athl Train. 2016.
40. Godin G, Jobin J, Bouillon J. Assessment of leisure time. exercise behavior by self-report: A concurrent validity study. Canadian Journal of Public Health. 1986; 77(5): 359-362.
41. Carcia C A, Martin R L, Drouin J M. Validity of the foot and ankle ability measure in athletes with chronic ankle instability. Journal of Athletic Training. 2008; 43(2):179-183.
42. Martin R L, Irrgang J J, Burdett R G, Conti S F, Van Swearingen J M. Evidence of validity for the foot and ankle ability measure (FRAM). Foot & Ankle International. 2003; 26(11):968-983.
43. Donahue M, Simon J, Docherty C L. Reliability and validity of a new questionnaire created to establish the presence of functional ankle instability: The IdFAI. Athl Train Sports Health Care. 2013; 5(1):38-43.
44. Hopkins W, Marshall S, Batterham A, Hanin J. Progressive statistics for studies in sports medicine and exercise science. Med Sci Sport Exerc. 2009; 41(1):3-13.
45. Cohen J. Statistical power analysis for the behavioral sciencies. Routledge; 1988.
46. McKeon P O, Paolini G, Ingersoll C D, et al. Effects of balance training on gait parameters in patients with chronic ankle instability: A randomized controlled trial. Clin Rehabil. 2009; 23 (7): 609-621.
47. Willems T, Witvrouw E, Delbaere K, De Cock A, De Clercq D. Relationship between gait biomechanics and inversion sprains: A prospective study of risk factors. Gait and Posture. 2005; 21(4):379-387.
48. Rice H, Nunns M, House C, Fallowfield J, Allsopp A, Dixon S. High medial plantar pressures during barefoot running are associated with increased risk of ankle inversion injury in royal marine recruits. Gait Posture. 2013; 38(4):614-618.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A gait device for rehabilitating or developing a subject's lower extremity, said device comprising:
    a movable belt configured for the subject to ambulate thereon;
    a track disposed above said movable belt generally aligned with said movable belt;
    a coupler that is configured to travel along said track and attach to the distal portion of the lower extremity of the subject while the subject is ambulating on said movable belt;
    wherein said distal portion of the lower extremity includes two ankles of the subject, lower portion of the two legs of the subject, and two feet of the subject;
    said track is positioned to be located between the two ankles, between the lower portion of the two legs, or between the two feet; and
    said coupler is configured to apply a medial force to the distal portion of the lower extremity during the ambulation to strengthen the ankle, knee and/or hip musculature of the subject.

2. The gait device of claim 1, wherein:
    said applied medial force is of varying degrees of force.

3. The gait device of claim 1, wherein said movable belt is motorized.

4. The gait device of claim 1, further comprising a sensor to determine movement of the subject.

5. The gait device of claim 4, wherein said sensor is disposed on the subject, apparel of the subject, and/or said gait device.

6. The gait device of claim 4, further comprising a processor or computer.

7. The gait device of claim 1, further comprising a processor or computer.

8. A method for rehabilitating or developing a gait of a subject's lower extremity, said method comprising:
    ambulating a subject on a movable belt;
    aligning a track with and above said movable belt; and
    coupling the distal portion of the lower extremity of the subject to the track while the subject is ambulating on said movable belt and while the coupling activity travels along said track;
    wherein said distal portion of the lower extremity includes two ankles of the subject, lower portion of the two legs of the subject, and two feet of the subject;
    said track is positioned to be located between the two ankles, between the lower portion of the two legs, or between the two feet; and
    said coupler is configured to apply a medial force to the distal portion of the lower extremity during the ambulation to strengthen the ankle, knee and/or hip musculature of the subject.

9. The method of claim 8, further comprising:
    varying the degree of the applied medial force.

* * * * *